(12) United States Patent
Seddon et al.

(10) Patent No.: US 9,597,206 B2
(45) Date of Patent: Mar. 21, 2017

(54) ANTI-MIGRATORY STENT COATING

(71) Applicant: Boston Scientific Scimed, Inc., Maple Grove, MN (US)

(72) Inventors: Dane T. Seddon, Boston, MA (US); Sean P. Fleury, Brighton, MA (US); Mark D. Wood, Shrewsbury, MA (US); Gary S. Kappel, Acton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/210,595

(22) Filed: Mar. 14, 2014

(65) Prior Publication Data
US 2014/0277442 A1 Sep. 18, 2014

Related U.S. Application Data

(60) Provisional application No. 61/798,897, filed on Mar. 15, 2013.

(51) Int. Cl.
*A61F 2/04* (2013.01)
*A61F 2/848* (2013.01)
*A61L 31/14* (2006.01)

(52) U.S. Cl.
CPC ............ *A61F 2/848* (2013.01); *A61F 2/04* (2013.01); *A61L 31/14* (2013.01); *A61F 2002/8483* (2013.01)

(58) Field of Classification Search
CPC ............ A61F 2/848; A61F 2002/8483; A61F 2002/8486
See application file for complete search history.

(56) References Cited

U.S. PATENT DOCUMENTS

| 3,221,746 A * | 12/1965 | Noble ............... A61B 17/11 |
|---|---|---|
| | | 285/239 |
| 5,059,169 A | 10/1991 | Zilber |
| 5,911,733 A | 6/1999 | Parodi |
| 8,114,147 B2 | 2/2012 | Wood et al. |

(Continued)

FOREIGN PATENT DOCUMENTS

GB 2164562 A * 3/1986 ............ A61B 17/11

OTHER PUBLICATIONS

PCT International Search Report, PCT International Application No. PCT/US2014/027813 (Filing Date: Mar. 14, 2014), mailed Jun. 2, 2014; 3 pgs.

(Continued)

*Primary Examiner* — Katrina Stransky
*Assistant Examiner* — Daniel Bissing
(74) *Attorney, Agent, or Firm* — Seager, Tufte & Wickhem, LLP

(57) ABSTRACT

The invention is directed to an anti-migratory stent comprising a tubular structure having an exterior surface and a plurality of protrusions provided on the exterior surface. The plurality of protrusions includes a first set of protrusions and a second set of protrusions. Each of the first and second set of protrusions includes a base and an apex. The apex of each of the first set of protrusions is offset from the base of the first set of protrusions in a direction opposite a direction of offset of the apex of each of the second set of protrusions from the base of the second set of protrusions.

17 Claims, 7 Drawing Sheets

(56) References Cited

U.S. PATENT DOCUMENTS

| | | | |
|---|---|---|---|
| 8,715,334 B2 | 5/2014 | Clerc et al. | |
| 2002/0010489 A1 | 1/2002 | Grayzel et al. | |
| 2003/0004535 A1 | 1/2003 | Musbach et al. | |
| 2003/0114915 A1 | 6/2003 | Mareiro et al. | |
| 2005/0113933 A1* | 5/2005 | Carter | A61F 2/07 623/23.7 |
| 2005/0125020 A1* | 6/2005 | Meade | A61B 17/0401 606/191 |
| 2006/0116754 A1* | 6/2006 | Thistle | A61B 17/064 623/1.36 |
| 2009/0187240 A1 | 7/2009 | Clerc et al. | |
| 2011/0040367 A1* | 2/2011 | Vinluan | A61F 2/07 623/1.13 |
| 2012/0035715 A1 | 2/2012 | Robida et al. | |
| 2012/0150274 A1 | 6/2012 | Shalev et al. | |
| 2013/0184808 A1* | 7/2013 | Hall | B32B 38/0036 623/1.22 |

OTHER PUBLICATIONS

PCT Written Opinion of the International Searching Authority, PCT International Application No. PCT/US2014/027813 (Filing Date: Mar. 14, 2014), mailed Jun. 2, 2014; 6 pgs.

* cited by examiner

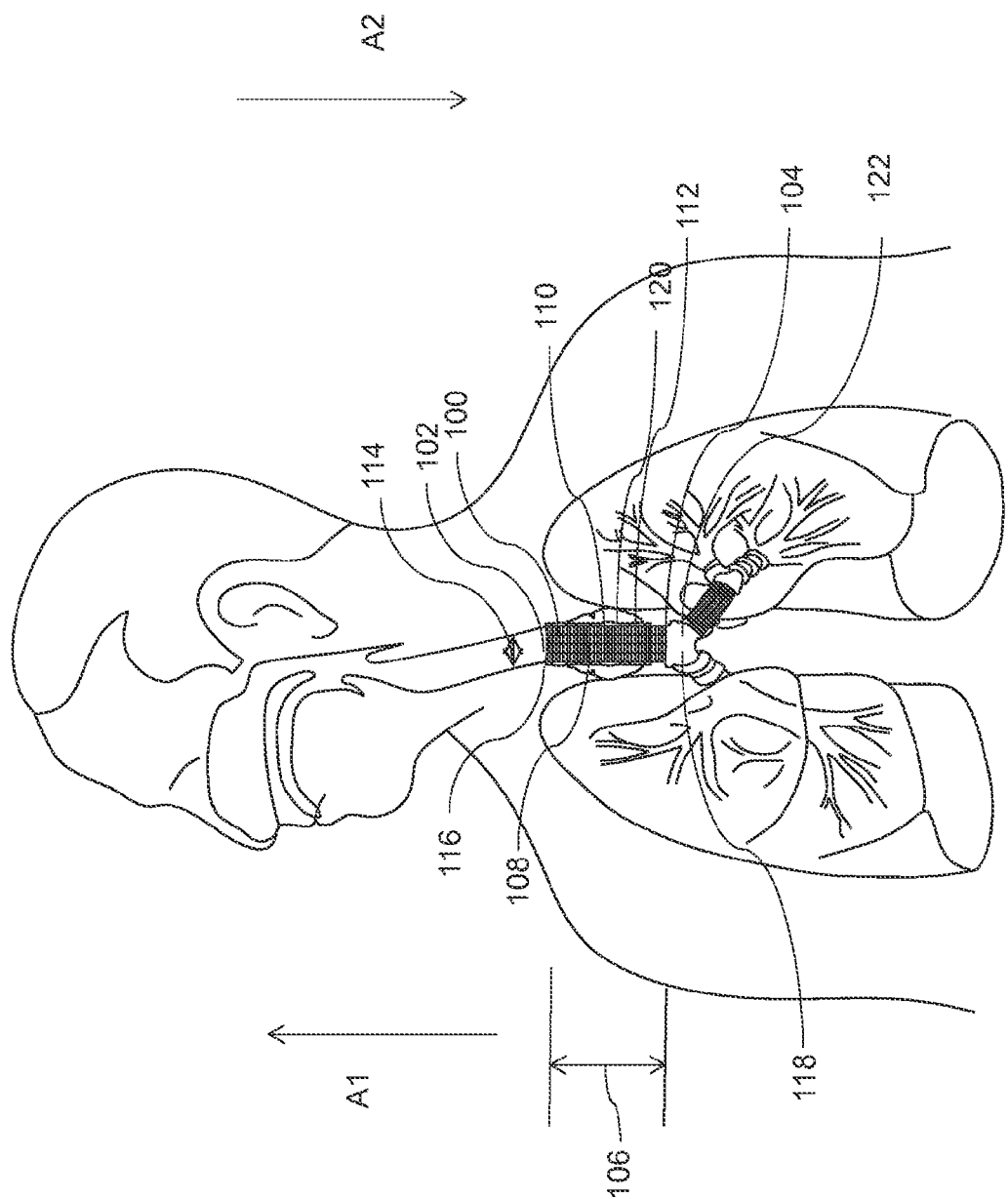

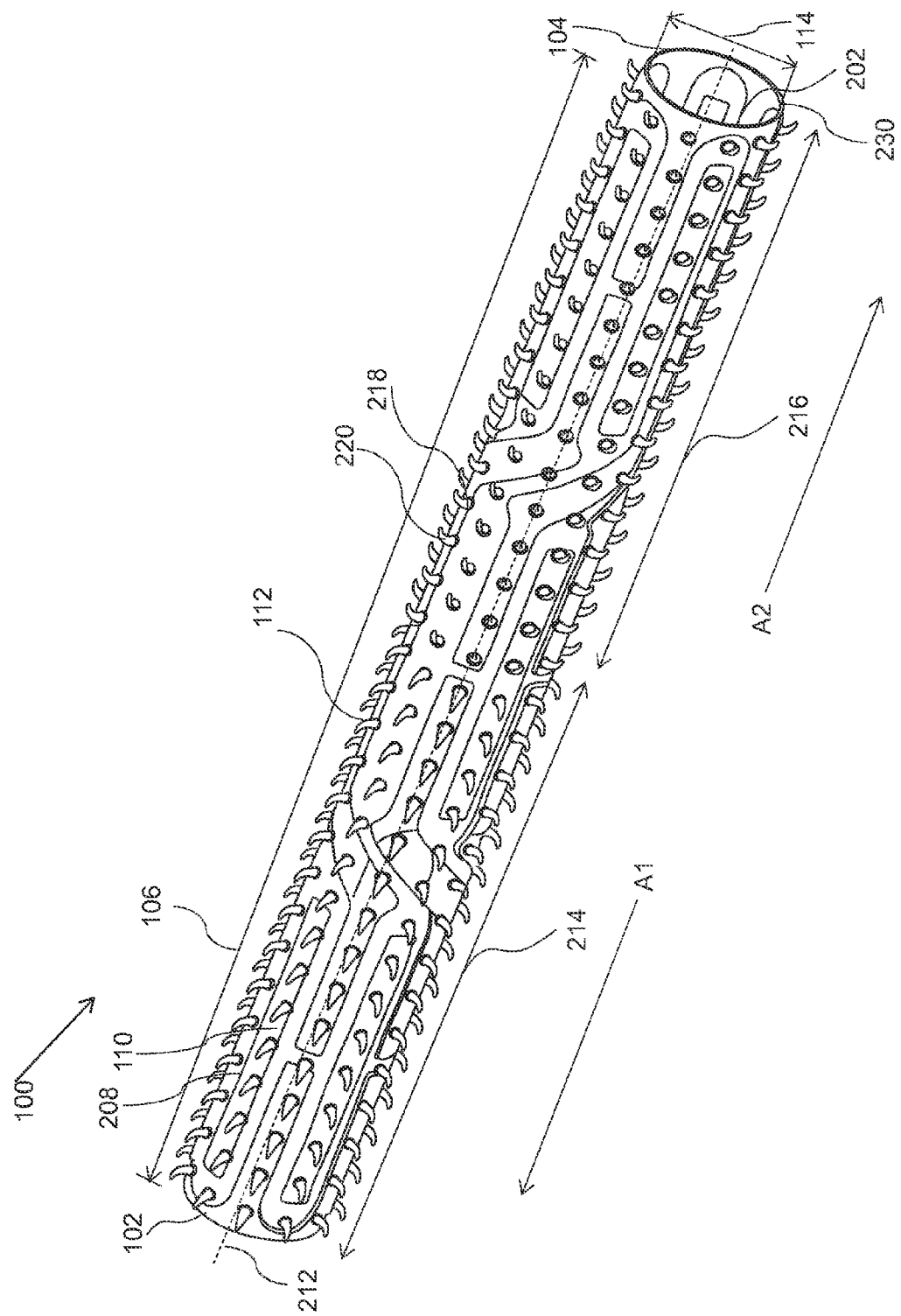

ANTI-MIGRATORY STENT COATING

CROSS REFERENCE TO RELATED APPLICATIONS

This application claims the benefit of provisional U.S. Patent Application Ser. No. 61/798,897 (entitled ANTI-MIGRATORY STENT COATING, filed on Mar. 15, 2013), which is hereby incorporated by reference in its entirety.

The following patent applications are incorporated herein by reference, each in its entirety:

U.S. Pat. App. Ser. No. 61/798,685 (Firstenberg et al.), entitled ANTI-MIGRATION MICROPATTERNED STENT COATING, filed on Mar. 15, 2013;

U.S. Pat. App. Ser. No. 61/798,794 (Clerc), entitled DELIVERY DEVICE FOR PARTIALLY UNCONSTRAINED ENDOPROSTHESIS, filed on Mar. 15, 2013;

U.S. Pat. App. Ser. No. 61/799,312 (Fleury et al.), entitled SUPERHYDROPHOBIC COATING FOR AIRWAY MUCUS PLUGGING PREVENTION, filed on Mar. 15, 2013;

U.S. Pat. App. Ser. No. 61/798,545 (Leanna et al.), entitled MEDICAL DEVICES HAVING MICROPATTERN, filed on Mar. 15, 2013; and U.S. Pat. App. Ser. No. 61/798,991 (Bertolino et al.), entitled BIOPSY TOOL HAVING MICROPATTERN, filed on Mar. 15, 2013.

FIELD

This disclosure relates to a medical device for removing blockages of target tissues. Particularly, it relates to a medical stent, which has features pertaining to migration of the stent from a target tissue to other adjoining areas.

BACKGROUND

Several types of implantable stents with different designs have been under significant development and made commercially available for use in providing mechanical scaffolding to hold body lumens open. These stents are generally used in body lumens, including particular blood vessels, and more specifically, coronary and peripheral arteries. One of the challenges that physicians may face with these stents is their migration.

Anti-migratory and radial force factors are interrelated and therefore, there are ways to avoid migration of stents by providing an additional radial force to the stent during its positioning inside the body passageways such as blood vessels. However, it is often found that increasing the radial force above a certain threshold results in minimal anti-migration gains, while significant increase in inflammation results in subsequent tissue granulation tissue. This can make the stent removal difficult and may cause irritation.

Other ways to reduce migration could be the use of fins. However, adding fins to prevent migration causes heightened levels of migration and also is not atraumatic.

Thus, there exists a need for a stent with a feature such as to increase the anti-migration ability of the stent.

Without limiting the scope of the invention, a brief summary of some of the claimed embodiments of the invention is provided below. Additional details of the summarized embodiments of the invention and/or additional embodiments of the invention can be found in the detailed description of the invention.

A brief abstract of the technical disclosure in the specification is provided as well for the purposes of complying with 37 C.F.R. 1.72. The abstract is not intended to be used for interpreting the scope of the claims.

All US patents and applications and all other published documents mentioned anywhere in this application are incorporated herein by reference in their entirety.

SUMMARY

In at least one embodiment, the invention is directed to an anti-migratory stent comprising a tubular structure having an exterior surface and a plurality of protrusions provided on the exterior surface. The plurality of protrusions includes a first set of protrusions and a second set of protrusions. Each of the first and second set of protrusions includes a base and an apex. The apex of each of the first set of protrusions is offset from the base of the first set of protrusions in a direction opposite a direction of offset of the apex of each of the second set of protrusions from the base of the second set of protrusions.

In at least one embodiment, the invention is directed to an anti-migratory stent comprising a tubular support structure having an exterior surface and a coating disposed about the exterior surface. The coating includes a plurality of protrusions. The plurality of protrusions includes a plurality of proximal-oriented protrusions and a plurality of distal-oriented protrusions. Each proximal-oriented protrusion has a base and an apex. The apex of each proximal-oriented protrusion is positioned at a predetermined radial distance from the base of the proximal-oriented protrusion. The apex of each proximal-oriented protrusion can be offset from the base of the proximal-oriented protrusion in a proximal direction. Each distal-oriented protrusion includes a base and an apex. The apex of each distal-oriented protrusion is positioned at a predetermined radial distance from the base of the distal-oriented protrusion. The apex of each distal-oriented protrusion can be offset from the base of the distal-oriented protrusion in a distal direction.

In at least one embodiment, the invention is directed to a method to increase an anti-migration ability of a stent. The method includes the steps of providing a generally tubular body having an internal surface defining a lumen therethrough, an external surface coaxially surrounding the internal surface, and a plurality of connecting channels that each defines an open passageway between the internal surface and the external surface. The method further includes providing an insert having an outer surface comprising a plurality of protrusions. Further, the method includes placing the insert within the lumen of the generally tubular body and orienting the insert so that the protrusions of the outer surface of the insert pass through the connecting channels of the generally tubular body and protrude beyond the external surface of the generally tubular body.

In at least one embodiment, the invention is directed to a method to increase an anti-migration ability of a stent. The method includes the steps of providing a generally tubular body having an internal surface defining a lumen therethrough, and an external surface coaxially surrounding the internal surface. The method further includes depositing a coating about the exterior surface, where the coating includes a first set of protrusions and a second set of protrusions. Each of the first and second set of protrusions includes a base and an apex. The apex of each of the first set of protrusions is offset from the base of the first set of protrusions in a direction opposite a direction of offset of the apex of each of the second set of protrusions from the base of the second set of protrusions.

BRIEF DESCRIPTION OF THE FIGURES

The invention and the following detailed description of certain embodiments thereof can be understood with reference to the following figures:

FIG. 1 is a perspective view of a system having a stent operationally positioned in a body of a patient.

FIG. 2A is a perspective view of a stent having an anti-migration ability.

DETAILED DESCRIPTION

Figure 2B:
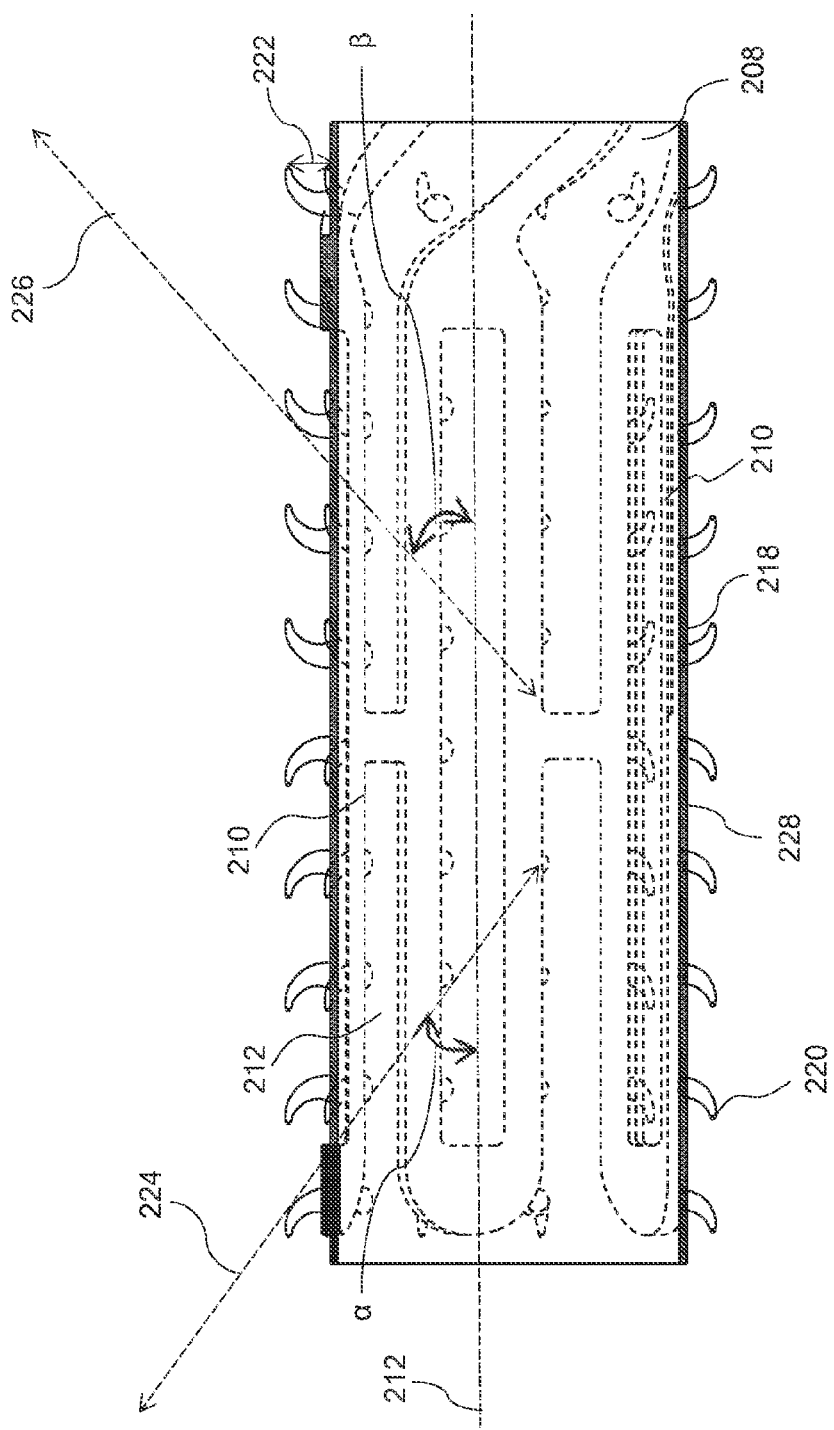
FIG. 2B is a partial cross-sectional view of the stent shown in FIG. 2A.

While this invention can be embodied in many different forms, specific embodiments of the invention are described in detail herein. This description is an exemplification of the principles of the invention and is not intended to limit the invention to the particular embodiments illustrated.

For the purposes of this disclosure, like reference numerals in the figures shall refer to like features unless otherwise indicated.

Various aspects of the invention are depicted in the figures. Elements depicted in one figure can be combined with and/or substituted for elements depicted in another figure as desired.

The terms proximal and distal described in relation to various devices, apparatuses, and components as discussed in the subsequent text of the present invention are referred with a point of reference. The point of reference, as used in this description, is a perspective of an operator. The operator can be a surgeon, a physician, a nurse, a doctor, a technician, and the like, who can perform the procedure of delivery and placement of the disclosed system/device into the patient's body as described in the present invention. The term proximal refers to an area or portion that is closer or closest to the operator during a placement procedure. The term distal refers to an area or portion that is further or farthest from the operator.

Referring now to FIG. 1, an anti-migratory stent 100 (also referred to as the stent 100) is illustrated. The stent has a proximal portion 102 and a distal portion 104. The stent includes a length 106 extending from the proximal portion 102 to the distal portion 106. The stent 100 includes a tubular structure 108 (also referred to as tubular body interchangeably) having an exterior surface 110 (also referred to as external surface 110 interchangeably). The stent 100 further includes a plurality of protrusions 112 (also referred to as raised features 112 interchangeably) on the exterior surface 110. The tubular structure 108 defines a width 114. In some embodiments, the width 114 is the same from the proximal portion 102 to the distal portion 104. In some embodiments, the width 114 may be different between the proximal portion 102 and the distal portion 104. The stent 100 can be used for performing a medical procedure at an internal treatment site 122 of a patient. The stent 100 is placed such that the proximal portion 102 of the stent 100 is proximate to a proximal portion 116 of the internal treatment site 122 and the distal portion 104 of the stent 100 is proximate to a distal portion 118 of the internal treatment site 122. In an embodiment, the stent 100 is positioned inside a patient's body to treat a lesion in a body passageway 120 of a patient. The stent 100 is generally flexible and/or elastomeric in nature such as to allow the stent 100 to be radially compressed for intraluminary catheter implantation. Once the stent 100 is properly positioned adjacent to a target body lumen, the stent 100 is radially expanded to support and reinforce the vessel. Radial expansion of the stent 100 may be accomplished by inflation of a balloon (not shown) attached to the catheter. In some embodiments, the stent 100 may be of a self-expanding type that can radially expand once deployed in the treatment site or the target body lumen.

As shown in FIG. 1, the stent 100 is capable of being placed in a body trachea or air passageways leading to lungs of the patient to open blockages present therein or facilitate air flow in the lungs. In an embodiment, the exterior surface 110 of the tubular structure 108 can be coated with drugs for targeted on site drug delivery. Although the stent 100 is shown to be positioned inside a trachea, those skilled in the pertinent art will quickly recognize that the stent 100 as described herein is not limited to the trachea, but can be used in an artery, vascular conduits, and other ductal systems such as a bile duct, a urinary tract, and the like in a human body. FIG. 1 shows the stent 100 used in a human body. It is to be appreciated that the medical system can also be used in non-humans such as animals, if desired. Functionally, the stent 100 is configured to expand or open a passageway to allow flow of materials or air inside a body of a patient. The stent 100 or some portions thereof can be fabricated using shape memory polymers or metals, or simple elastic medical grade polymers, or medical grade plastically expendable materials.

FIG. 2A illustrates a perspective view of the stent 100. FIG. 2B illustrates a partial cross-sectional view of the stent 100.

Referring now to FIGS. 2A and 2B, the stent 100 includes the tubular body 108, a lumen 202 defined therethrough between the proximal portion 102 and the distal portion 104 of stent 100, and the plurality of protrusions 112 on the exterior surface 110 of the tubular body 108. The tubular body 108 includes an interior surface 230 (also referred to as internal surface interchangeably) and a plurality of channels 208 extending from the interior surface 230 to the exterior surface 110. The interior surface 230 defines the lumen 202. Each of the plurality of channels 208 can be configured to define an open passageway 210 between the exterior surface 110 and the interior surface 230 (as illustrated in FIG. 2B). Each of the plurality of channels 208 can be fabricated so that the plurality of protrusions 112 can pass from the interior surface 230 to the exterior surface 110 through open passageway 210 fabricated in the plurality of channels 208. This can be accomplished through processes such as microblasting, sanding, PTFE mold features that can fit inside the plurality of channels 208 and protrudes through the open passageway 210. The exterior surface 110 can be configured to coaxially surround the interior surface 230 around a longitudinal axis 212 such that the exterior surface 110 can be in contact with at least a portion of the internal treatment site 122. The plurality of protrusions 112 includes a first set of protrusions 214 and a second set of protrusions 216. Each of the first and second set of protrusions 214 and 216 includes a base 218 and an apex 220. The apex 220 of each of the protrusion is positioned at a predetermined radial distance 222 from the base 218 of that protrusion (as illustrated in FIG. 2B). The pre-determined radial distance is the same for each of the first and second set of protrusions 214 and 216. In some embodiments, the base 218 can have a circular shape. In other embodiments, the base 218 can have a different shape than a circular shape. In some embodiments, the base 218 can have a polygon shape. For example, the base 218 can have a square or a rectangular shape or profile. In some embodiments, the apex 220 can have a conical shape or profile. In some embodiments, the apex 220 can have a tapered profile. In an embodiment, the apex 220 of each of the first set of protrusions 214 is offset from the base 218 of the first set of protrusions 214 in a direction A1 opposite a direction A2 of offset of the apex 220 of each of the second set of protrusions 216 from the base 218 of the second set of protrusions 216. The direction A1 may be referred to as a proximal direction and the direction A2 may be referred to as a distal direction. The opposite direction offset increases the anti-migratory properties of the stent 100 as the proximal-oriented protrusions placed at the distal portion 104 and pointing in the proximal direction can hold onto the distal portion 118 of the internal treatment site 122 and the distal-oriented protrusions placed at the proximal portion 102 and pointing in the distal direction can hold onto the proximal portion 116 of the internal treatment site 122. The plurality of distal-oriented protrusions facilitate coupling of the stent 100 at the proximal portion 116 of the internal treatment site 122 and the plurality of proximal-oriented protrusions facilitate coupling of the stent 100 at the distal portion 118 of the internal treatment site 122, thereby creating a mechanical lock against movement or migration of the stent 100. Each of the apex 220 of the plurality of the proximal-oriented protrusions 214 and the plurality of the distal-oriented protrusions 216 can function as anchoring points to key into the vessel walls (cartilage rings) and help reduce migration potential. The plurality of protrusions 112 can provide added frictional interaction between the exterior surface 110 of the stent 100 and the vessel walls, thereby facilitating anti-migration functionality and preventing the movement of the overall stent 100 inside vessel walls. The plurality of protrusions 112 can be fabricated to accommodate various tolerances in the stent 100 delivery systems, for example, placement by radial compressions or placement by ballooning.

In some embodiments, the apex 220 can be offset in the direction A1 toward the proximal portion 102 of the stent 100. The plurality of protrusions 112 offset in the direction A1 toward the proximal portion 102 of the stent 100 can be referred to as a plurality of proximal-oriented protrusions or the first set of protrusions 214. In some embodiments, the apex 220 can be offset in the direction A2 toward the distal portion 104 of the stent 100. The plurality of protrusions 112 offset in the direction A2 toward the distal portion 104 can be referred to as a plurality of distal-oriented protrusions or the second set of protrusions 216. In some embodiments, the proximal-oriented protrusions can be present around the distal portion 104 of the stent 100 and the distal-oriented protrusions can be present around the proximal portion 102 of the stent 100 as illustrated in FIG. 2A. In other embodiments, the proximal-oriented protrusions can be present around the proximal portion 102 of the stent 100 and the distal-oriented protrusions can be present around the distal portion 104 of the stent 100.

In some embodiments, the plurality of protrusions 112 can be present around the proximal portion 102 and distal portion 104 of the stent 100 only. In an embodiment, the plurality of protrusions 112 can be provided over an entire length 106 of the tubular structure 108 and can be configured to completely surround the longitudinal axis 212 of the tubular structure 108. In some embodiments, the exterior surface 110 may be designed to be fairly smooth and the plurality of protrusions 112 may be coupled as a separate structure to the exterior surface 110.

Each of the first set of protrusions 214 can be offset from the base 218 at a first offset angle α and the second set of protrusions 216 can be offset from the base 218 at a second angle β (as illustrated in FIG. 2B). The first offset angle α is formed between a plane 224 of the apex 220 of each protrusion of the first set of protrusions 214 and the longitudinal axis 212. The second offset angle β is formed between a plane 226 of the apex 220 of each protrusion of the second set of protrusions 216 and the longitudinal axis 212. In some embodiments, the first offset angle α can be equal to the second offset angle β. The degree of the first offset angle α and the second offset angle β can be varied, depending upon the size of the internal treatment site 122, structure of the internal treatment site 122, and the contour of the internal treatment site 122.

In an embodiment, a coating 228 is disposed about the exterior surface 110 such that the coating 228 includes the plurality of protrusions 112 (as illustrated in FIG. 2B). In an embodiment, the coating 228 can be formed by techniques, such as for example, a dip coating technique, an air spraying technique, or any other technique. In some embodiments, the coating 228 may define a three-dimensional (3D) geometric structure that includes the plurality of protrusions 112. When formed as a 3D structure, the stent 100 can be imparted an uneven contoured irregularity over the exterior surface 110, which may act as a friction point, thereby enhancing the anti-migratory ability of the stent 100. In an embodiment, the uneven irregularity can be defined in the form of wave like structures with peaks and troughs. In other embodiment, several other types of profiles constituting irregularities can be generated over the exterior surface 110 by deposition of the coating 228. In some embodiments, the plurality of protrusions 112 can be developed over the exterior surface 110 in the form of the coating 228 using computer controlled spraying equipment to develop a specific profile. In some embodiments, the coating 228 can include two layers—a first layer comprising the plurality of protrusions 112 developed over the exterior surface 110 and a second layer comprising a therapeutic compound for targeted on site drug delivery. In some embodiments, the plurality of protrusions 112 can be mold casted and inserted into the tubular body 108 and the coating 228 can comprise a therapeutic agent for targeted on site drug delivery. In some embodiments, each of the plurality of protrusions 112 can be fabricated so that they are individually rigid and elastically flexible so as to facilitate mechanical locking of the plurality of protrusions 112 with the vessel walls.

In some embodiments, the plurality of protrusions 112 can be cast formed or molded on the tubular structure 108 or on the coating 228 disposed about the exterior surface 110 of the tubular structure 108. In some embodiments, the plurality of protrusions 112 can be injection molded or vacuum cast. In some embodiments, the plurality of protrusions 112 can be pre-formed and inserted through the lumen 202 such as to pass through the open passageways and extend from the exterior surface 110 of the tubular structure 108. In some embodiments, the plurality of protrusions 112 can include an array of hooks with a curved profile from the base 218 to the apex 220 of each of the protrusions. In some embodiments, the plurality of protrusions 112 can be barb-shaped. In some embodiments, the plurality of protrusions 112 can be barb-shaped having the base 218 that is circular in shape and an apex 220 that is conical in shape. In some embodiments, the plurality of protrusions 112 can be in the form of peaks and valleys directly formed or provided on the tubular structure 108 or formed on the coating 228 or as an integral part of the coating 228 on the exterior surface 110.

In an embodiment, the plurality of protrusions 112 can be made from a polymeric material made of, such as for example, silicone, nylon, polyamide, polyurethane, polyethylene, terephthalate, polypropylene, polytetrafluoroethylene (PTFE), expanded polytetrafluoroethylene, and combinations thereof.

In some embodiments, the plurality of protrusions 112 is triangular in shape. In some embodiments, the shape of the first set of protrusions 214 can be the same as the shape of the second set of protrusions 216. In other embodiments, the shape of the first set of protrusions 214 can be different from the shape of the second set of protrusions 216. The plurality of protrusions 112 can have any shape that can facilitate biasing the first set of protrusions 214 in any one of the directions A1 or A2 and biasing the second set of protrusions 216 in a direction opposite to the biasing direction of the first set of protrusions 214. The first offset angle can be used to influence the biasness of the first set of protrusions 214. In some embodiments, the first offset angle can be an acute angle, thereby biasing the first set of protrusions 214 along the direction A1. In some embodiments, the first offset angle can be an obtuse angle, thereby biasing the first set of protrusions 214 along the direction A2. The second offset angle can be used to influence the biasness of the second set of protrusions 216. In some embodiments, the second offset angle can be an acute angle, thereby biasing the second set of protrusions 216 along the direction A2. In some embodiments, the second offset angle can be an obtuse angle, thereby biasing the second set of protrusions 216 along the direction A1.

In most of the cases, the stent 100 would be fabricated in such a shape that it can be placed inside the body so that it interacts with the vessel walls along the longitudinal axis 212. Therefore, if the movement of the stent 100 along the directions A1 and A2 are prevented, the stent 100 would be held in place.

Figure 3A:
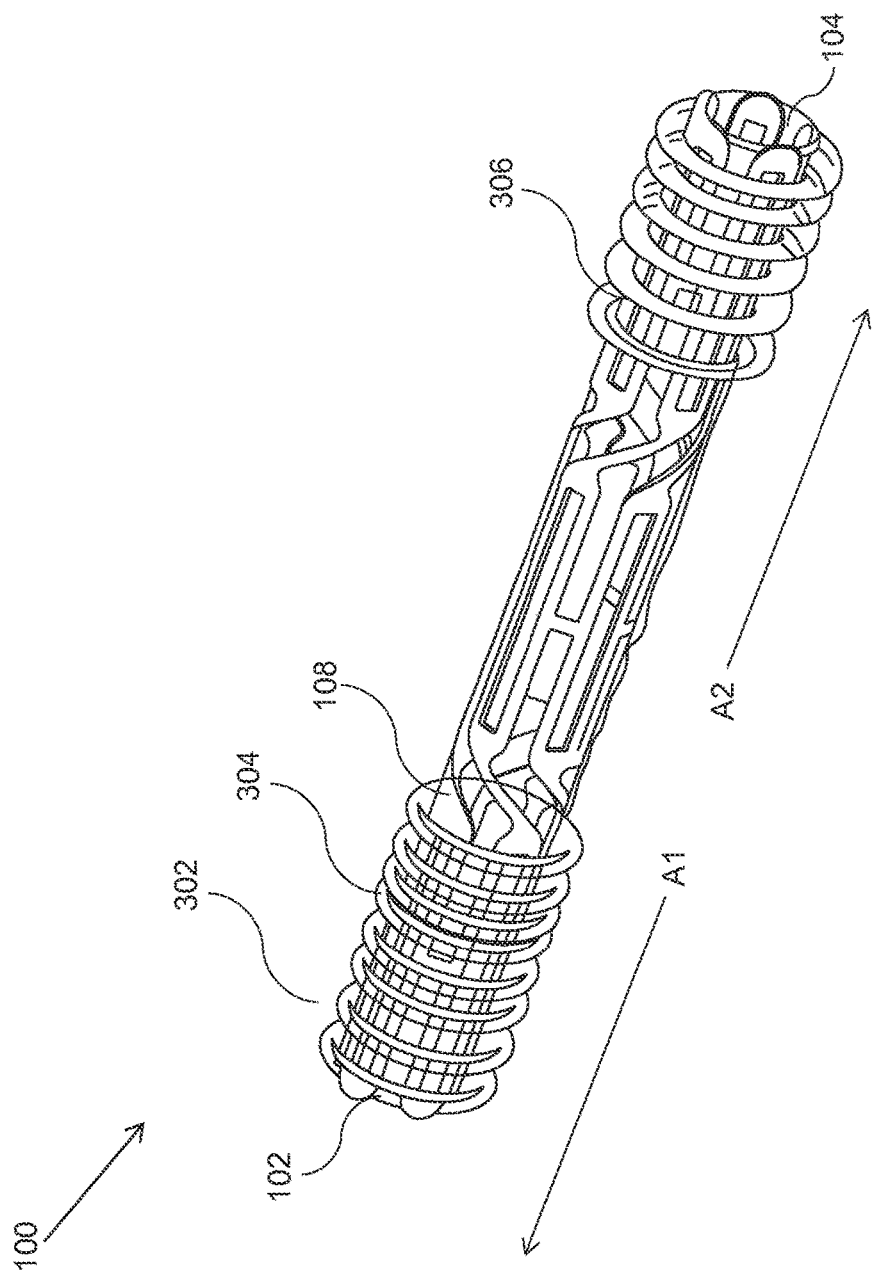
FIG. 3A is a perspective view of a stent, in accordance with an exemplary embodiment of the invention.
Figure 3B:
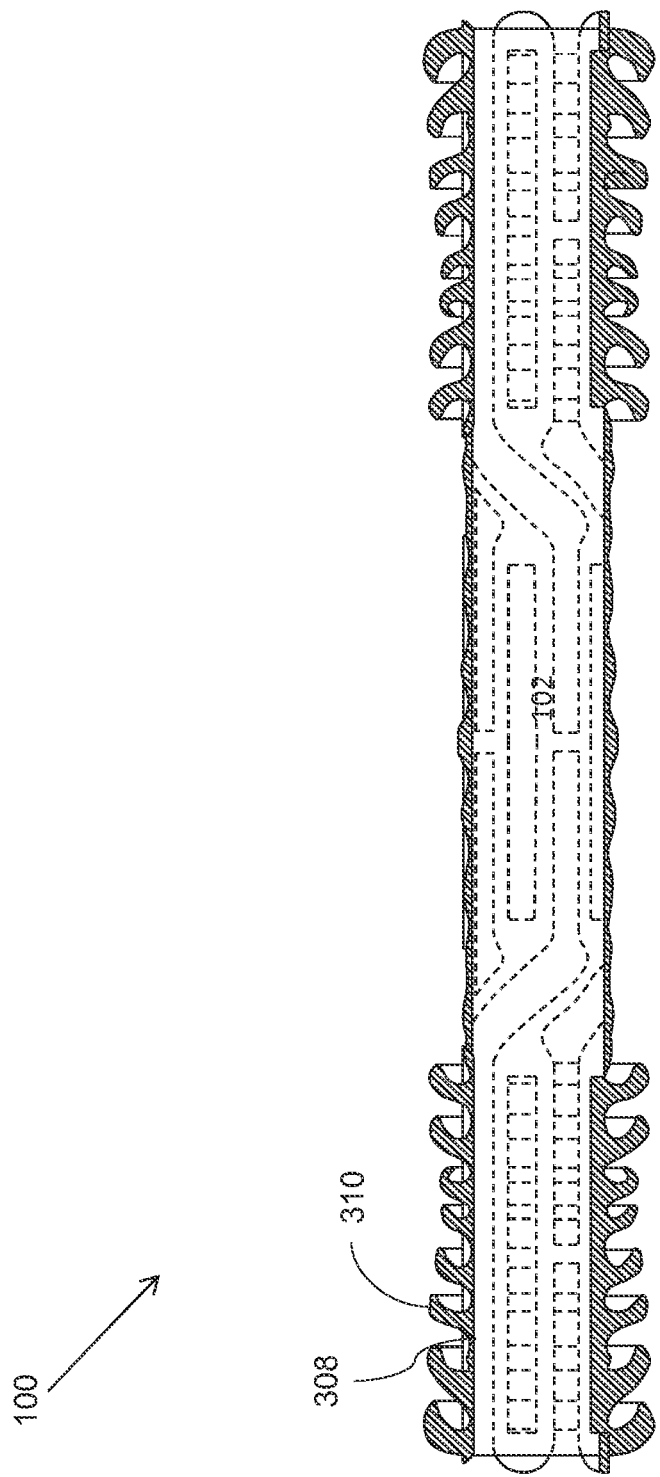
FIG. 3B is a cross sectional view of the stent shown in FIG. 3A.

FIG. 3A illustrates a perspective view of the stent 100 with a wave profile. FIG. 3B illustrates a cross-sectional view of the stent 100 such as shown in FIG. 3A. FIGS. 3A and 3B show the plurality of protrusions 112 over a portion of the length 106 of the tubular structure 108 as opposed to over the entire length 106 as shown in FIGS. 2A and 2B.

Referring now to FIGS. 3A and 3B, in some embodiments, the exterior surface 110 includes a wave profile 302. The wave profile 302 includes a plurality of crests 304 and a plurality of troughs 306. The plurality of crests 304 and troughs 306 defines projections that serve as the plurality of protrusions 112, including the first set of protrusions 214 and the second set of protrusions 216. Each of the plurality of crests 304 can include a proximal portion 308 and a distal portion 310 such that the proximal portion 308 is in contact with the exterior surface 110 of the tubular structure 108 and the distal portion is offset towards the directions A1 or A2. In some embodiments, the plurality of crests 304 proximate to the proximal portion 102 of the stent 100 point in the distal direction (A2) and the plurality of crests 304 proximate to the distal portion 104 of the stent 100 point in the proximal direction (A1). In other embodiments, the plurality of crests 304 proximate to the proximal portion 102 of the stent 100 can point in the proximal direction (A1) and the plurality of crests 304 proximate to the distal portion 104 of the stent 100 can point in the distal direction (A2). The plurality of crests 304 at opposite directions and pointing in the opposite directions create a mechanical lock, thereby decreasing migration potential of the stent 100. The plurality of protrusions 112 or the plurality of crests 304 along with the plurality of troughs 306 mechanically gets coupled into the cartilage rings or any other adjoining areas of the internal treatment site 122 to increase the anti-migration potential of the stent 100.

Figure 4:
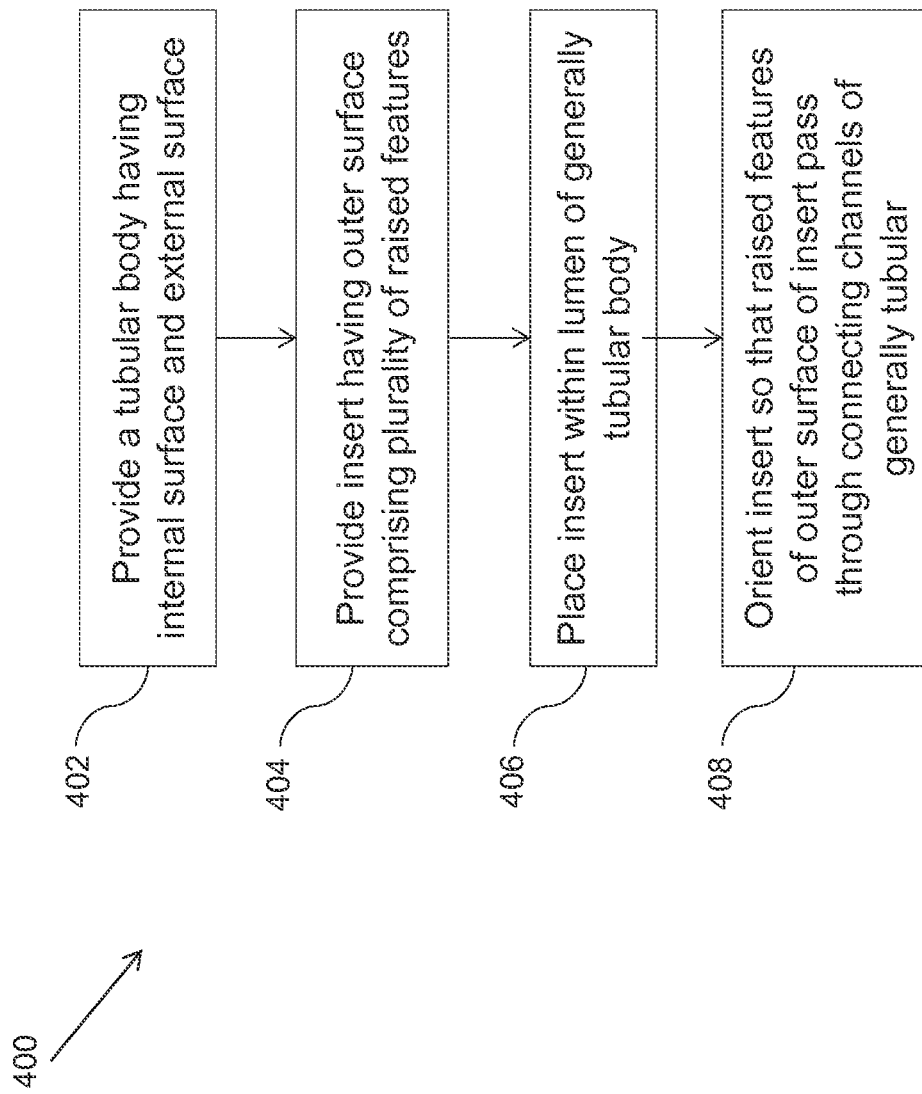
FIG. 4 is a flow chart illustrating a method for increasing anti-migration ability of a stent.

FIG. 4 is a flow chart illustrating a method 400 for increasing the anti-migration ability of the stent 100. At 402, the method 400 can include fabricating a generally tubular body 108 having an internal surface similar to the interior surface 230 defining a lumen similar to the lumen 202 therethrough, and an external surface similar to the exterior surface 110 coaxially surrounding the internal surface of the stent 100. The method 400 further includes fabricating a plurality of connecting channels between the exterior surface 110 and the internal surface. In some embodiments, each of the connecting channels defines an open passageway between the internal surface and the exterior surface 110. At 404, the method 400 includes fabricating an insert having an outer surface. The outer surface of the insert includes the plurality of raised features (the plurality of protrusions 112). At 406, the method further includes placing the insert within the lumen 202 of the tubular body 108. The insert is placed inside the lumen 202 of the tubular body 108 such that the insert passes through the plurality of connecting channels into the open passageways. At 408, the method 400 includes orienting the insert so that the raised features of the outer surface of the insert passes through the connecting channels 208 of the generally tubular body 108 and protrude beyond the exterior surface 110 of the generally tubular body 108. This leads to formation of the plurality of protrusions 112 over the exterior surface 110. In some embodiments, the plurality of protrusions 112 can be coated with a therapeutic material.

Figure 5:
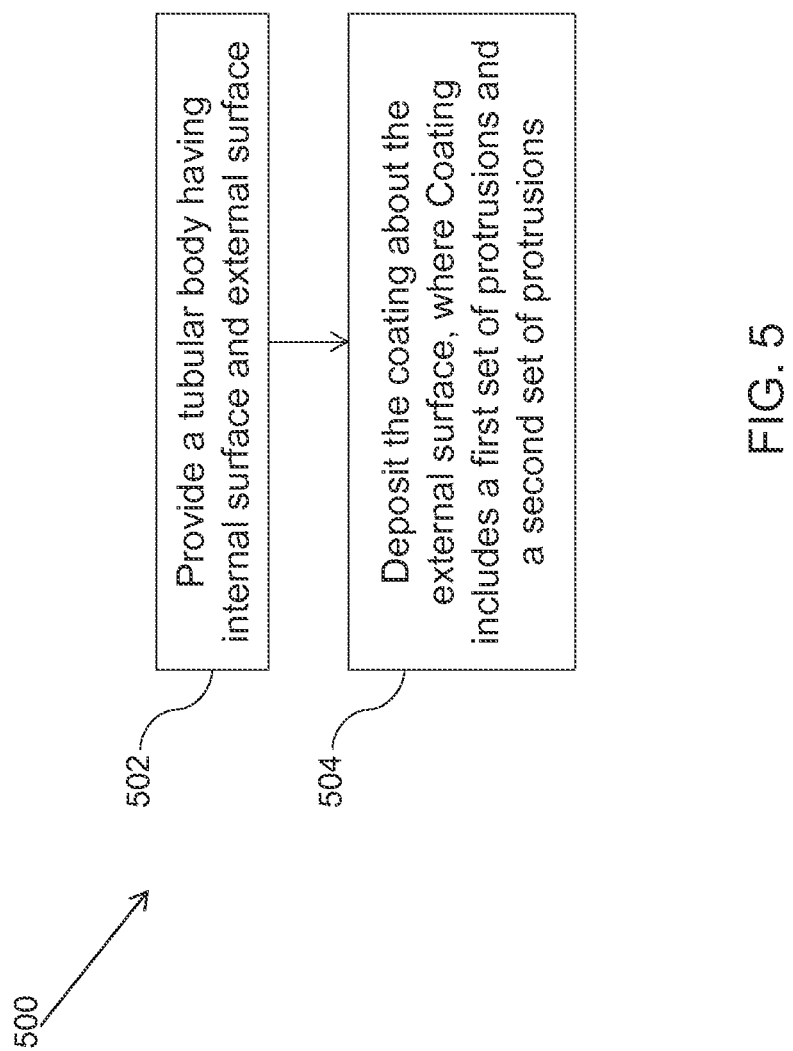
FIG. 5 is a flow chart illustrating a method for coating a stent.

FIG. 5 is a flow chart illustrating a method 500 for increasing the anti-migration ability of the stent 100. At 502, the method includes providing the generally tubular body 108 having the internal surface defining the lumen 202 therethrough, and the exterior surface 110 coaxially surrounding the internal surface. At 504, the method includes depositing the coating 228 about the exterior surface 110. The coating 228 includes the first set of protrusions 214 and the second set of protrusions 216. Each of the first and second set of protrusions 214 and 216 includes the base 218 and the apex 220. The apex 220 of each of the first set of protrusions 214 is offset from the base 218 of the first set of protrusions 214 in a direction opposite to a direction of offset of the apex 220 of each of the second set of protrusions 216 from the base 218 of the second set of protrusions 216. In some embodiments, the coating 228 can be formed by one of a dip coating 228 and an air spraying technique or any other technique.

A description of some exemplary embodiments of the invention can be contained in the following numbered statements:

1. An anti-migratory stent comprising:
   a tubular structure having an exterior surface; and
   a plurality of protrusions provided on the exterior surface and comprising a first set of protrusions and a second set of protrusions, each of the first and second set of protrusions having a base and an apex, the apex of each of the first set of protrusions being offset from the base of the first set of protrusions in a direction opposite a direction of offset of the apex of each of the second set of protrusions from the base of the second set of protrusions.

2. The stent of statement 1 where at least one of the plurality of protrusions is made from a polymeric material selected from a group consisting of silicone, nylon, polyamide, polyurethane, polyethylene, terephthalate, polypropylene, polytetrafluoroethylene, expanded polytetrafluoroethylene, and combinations thereof.

3. The stent of statement 1 or statement 2 where at least one of the plurality of protrusions is barb-shaped, having a base that is circular in shape and an apex that is conical in shape.

4. The stent of statement 1 or statement 2 where at least one of the plurality of protrusions completely surrounds a longitudinal axis of the tubular support structure.

5. The stent of any one of statements 1-4 further comprising a coating disposed about the exterior surface and the coating having the plurality of protrusions.

6. The stent of statement 5 where the plurality of protrusions are cast formed or molded on the coating disposed about the exterior surface.

7. The stent of statement 5 where the coating is formed by one of a dip coating and an air spraying technique.

8. The stent of statement 1 where the plurality of protrusions are injection molded or vacuum cast.

9. The stent of any one of statements 1-8 where the plurality of protrusions comprises an array of hooks with a curved profile from the base to the apex of each of the protrusions.

10. The stent of any one of statements 1-9 wherein the apex of each of the first and second set of protrusions is positioned a predetermined radial distance from the base of the plurality of protrusions.

11. An anti-migratory stent comprising:
a tubular support structure having an exterior surface; and
a coating disposed about the exterior surface, the coating having a plurality of protrusions, the plurality of protrusions comprising a plurality of proximal-oriented protrusions and a plurality of distal-oriented protrusions,
each proximal-oriented protrusion having a base and an apex, the apex of each proximal-oriented protrusion being positioned a predetermined radial distance from the base of the proximal-oriented protrusion, the apex of each proximal-oriented protrusion being offset from the base of the proximal-oriented protrusion in a proximal direction,
each distal-oriented protrusion having a base and an apex, the apex of each distal-oriented protrusion being positioned a predetermined radial distance from the base of the distal-oriented protrusion, the apex of each distal-oriented protrusion being offset from the base of the distal-oriented protrusion in a distal direction.

12. The stent of statement 11 where the plurality of protrusions are cast formed or molded on the coating disposed about the exterior surface.

13. The stent of statement 11 where the coating is formed by one of a dip coating and an air spraying technique.

14. A method to increase an anti-migration ability of a stent, the method comprising the steps of:
providing a generally tubular body having an internal surface defining a lumen therethrough, an external surface coaxially surrounding the internal surface, and a plurality of connecting channels that each define an open passageway between the internal surface and the external surface;
providing an insert having an outer surface comprising a plurality of protrusions;
placing the insert within the lumen of the generally tubular body;
orienting the insert so that the protrusions of the outer surface of the insert pass through the connecting channels of the generally tubular and protrude beyond the external surface of the generally tubular body.

15. The method of statement 14 where at least one of the protrusions of the insert is made from a polymeric material selected from a group consisting of silicone, nylon, polyamide, polyurethane, polyethylene, terephthalate, polypropylene, polytetrafluoroethylene, expanded polytetrafluoroethylene, and combinations thereof.

16. The method of statement 14 or statement 15 where the protrusions are triangular in shape.

17. The method of any one of statements 14-16 where the protrusions are wave-shaped.

18. The method of any one of statements 14-17 where the protrusions are constructed and arranged to key into structure of a wall of a body lumen.

19. The method of statement 18 wherein the structure comprises cartilage rings.

20. The method of statement 18 wherein the body lumen comprises a trachea or an airway.

21. A method to increase an anti-migration ability of a stent, the method comprising the steps of:
providing a generally tubular body having an internal surface defining a lumen therethrough, and an external surface coaxially surrounding the internal surface; and
depositing a coating about the exterior surface, where the coating comprising a first set of protrusions and a second set of protrusions, each of the first and second set of protrusions having a base and an apex, the apex of each of the first set of protrusions being offset from the base of the first set of protrusions in a direction opposite a direction of offset of the apex of each of the second set of protrusions from the base of the second set of protrusions.

22. The stent of statement 21, where the coating is formed by one of a dip coating and an air spraying technique.

The above disclosure is intended to be illustrative and not exhaustive. This description will suggest many variations and alternatives to a person of ordinary skill in this art. The various elements shown in the individual figures and described above can be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art can recognize other equivalents to the specific embodiment described herein which equivalents are intended to be encompassed by the claims attached hereto.

The invention claimed is:

1. An anti-migratory stent comprising:
an expandable tubular support structure having an exterior surface, an interior surface, and a plurality of channels extending from the interior surface to the exterior surface;
a coating disposed about the exterior surface and extending across the plurality of channels; and
a plurality of protrusions extending from an outer surface of the coating, the plurality of protrusions comprising a first set of protrusions adjacent the proximal end and a second set of protrusions adjacent the distal end, each of the first and second set of protrusions having a base and an apex, the apex of each of the first set of protrusions being offset from the base of the first set of protrusions in a direction opposite a direction of offset of the apex of each of the second set of protrusions from the base of the second set of protrusions;
wherein the plurality of protrusions are cast formed or molded on the coating.

2. The stent of claim 1 wherein at least one of the plurality of protrusions is made from a polymeric material selected from a group consisting of silicone, nylon, polyamide, polyurethane, polyethylene, terephthalate, polypropylene, polytetrafluoroethylene, expanded polytetrafluoroethylene, and combinations thereof.

3. The stent of claim 1 wherein at least one of the plurality of protrusions is barb-shaped, having a base that is circular in shape and an apex that is conical in shape.

4. The stent of claim 1 wherein along at least some portion of the stent the plurality of protrusions completely surrounds a longitudinal axis of the tubular support structure.

5. The stent of claim 1 wherein the plurality of protrusions extend through the plurality of channels of the tubular support structure.

6. The stent of claim 1 wherein the plurality of protrusions are injection molded or vacuum cast.

7. The stent of claim 1 wherein the plurality of protrusions comprises an array of hooks with a curved profile from the base to the apex of each of the protrusions.

8. The stent of claim 1 wherein the apex of each of the first and second set of protrusions is positioned a predetermined radial distance from the base of the plurality of protrusions.

9. An anti-migratory stent comprising:
an expandable tubular support structure having an exterior surface, an interior surface, and a plurality of channels extending from the interior surface to the exterior surface; and
a coating disposed about the exterior surface, the coating having a plurality of protrusions, the plurality of protrusions comprising a plurality of proximal-oriented protrusions disposed adjacent the proximal end and a plurality of distal-oriented protrusions disposed adjacent the distal end,
each proximal-oriented protrusion having a base and an apex, the apex of each proximal-oriented protrusion being positioned a predetermined radial distance from the base of the proximal-oriented protrusion, the apex of each proximal-oriented protrusion being offset from the base of the proximal-oriented protrusion in a proximal direction,
each distal-oriented protrusion having a base and an apex, the apex of each distal-oriented protrusion being positioned a predetermined radial distance from the base of the distal-oriented protrusion, the apex of each distal-oriented protrusion being offset from the base of the distal-oriented protrusion in a distal direction;
wherein the plurality of protrusions are cast formed or molded on the coating.

10. The stent of claim 1, wherein the apex of the first set of protrusions faces the proximal end and the apex of the second set of protrusions faces the distal end.

11. An anti-migratory stent comprising:
an expandable tubular support structure having an exterior surface, an interior surface, and a plurality of channels extending from the interior surface to the exterior surface;
a coating disposed about the exterior surface and extending across the plurality of channels, the coating including a plurality of protrusions formed integrally with and extending from an outer surface of the coating;
wherein the plurality of protrusions comprise a first set of protrusions adjacent the proximal end and a second set of protrusions adjacent the distal end, each of the first and second set of protrusions having a base and an apex, the apex of each of the first set of protrusions being offset from the base of the first set of protrusions in a direction opposite a direction of offset of the apex of each of the second set of protrusions from the base of the second set of protrusions.

12. The stent of claim 11 wherein at least one of the plurality of protrusions is made from a polymeric material selected from a group consisting of silicone, nylon, polyamide, polyurethane, polyethylene, terephthalate, polypropylene, polytetrafluoroethylene, expanded polytetrafluoroethylene, and combinations thereof.

13. The stent of claim 11 wherein at least one of the plurality of protrusions is barb-shaped, having a base that is circular in shape and an apex that is conical in shape.

14. The stent of claim 11 wherein along at least some portion of the stent the plurality of protrusions completely surrounds a longitudinal axis of the tubular support structure.

15. The stent of claim 11 wherein the plurality of protrusions extend through the plurality of channels of the tubular support structure.

16. The stent of claim 11 wherein the plurality of protrusions comprises an array of hooks with a curved profile from the base to the apex of each of the protrusions.

17. The stent of claim 11 wherein the apex of each of the first and second set of protrusions is positioned a predetermined radial distance from the base of the plurality of protrusions.

* * * * *